United States Patent [19]

Knoll et al.

[11] 4,281,382
[45] * Jul. 28, 1981

[54] RADIATION SIGNAL PROCESSING SYSTEM

[75] Inventors: Glenn F. Knoll, Ann Arbor; Donald R. Strange, Howell; Matthew C. Bennett, Jr., Ann Arbor, all of Mich.

[73] Assignee: Medtronic, Inc., Minneapolis, Minn.

[*] Notice: The portion of the term of this patent subsequent to Jul. 8, 1997, has been disclaimed.

[21] Appl. No.: 99,691

[22] Filed: Dec. 3, 1979

Related U.S. Application Data

[63] Continuation of Ser. No. 862,889, Dec. 21, 1977, Pat. No. 4,212,061.

[51] Int. Cl.³ .......................... G06F 7/38; G01T 1/20
[52] U.S. Cl. .............................. 364/414; 250/363 S; 364/515; 364/571
[58] Field of Search ............... 364/414, 527, 515, 571, 364/582; 250/363 S, 363 R, 315 R, 315 A, 361

[56] References Cited

U.S. PATENT DOCUMENTS

| | | | |
|---|---|---|---|
| 3,732,419 | 5/1973 | Kulberg et al. | 250/363 S |
| 3,732,420 | 5/1973 | Brunnet et al. | 250/363 S |
| 3,852,598 | 12/1974 | Larsson | 250/363 S |
| 3,882,304 | 5/1975 | Walters | 364/723 |
| 3,919,556 | 11/1975 | Berninger | 250/363 S |
| 3,993,908 | 11/1976 | Kaplan et al. | 364/414 |
| 4,055,765 | 10/1977 | Gerber et al. | 250/363 S |
| 4,060,730 | 11/1977 | Zioni et al. | 250/363 S |
| 4,066,903 | 1/1978 | Le May | 250/363 S |
| 4,093,857 | 6/1978 | Lapidus | 250/363 S |
| 4,212,061 | 7/1980 | Knoll et al. | 364/414 |

FOREIGN PATENT DOCUMENTS

| | | | |
|---|---|---|---|
| 2325054 | 4/1977 | France | 250/363 S |
| 1370084 | 10/1974 | United Kingdom | 250/363 S |
| 1432870 | 4/1976 | United Kingdom | 250/363 S |

OTHER PUBLICATIONS

Brunsden et al.; "A Continuously Variable Line Phantom For Quality Assurance;" vol. I, 1977, IAEA, Vienna, AT; Medical Rad. Imaging.

Primary Examiner—Errol A. Krass
Attorney, Agent, or Firm—Carl A. Forest; Lew Schwartz; Joseph F. Breimayer

[57] ABSTRACT

A gamma ray scintillation camera generating (X,Y) spatial coordinate and Z energy signals relative to detected radiation events. The system provides for calibration of the camera Z signal response as a function of camera face location. In addition, the camera signals are converted to their digital equivalents subsequent to which the apparent coordinate locations of detected events as determined by the camera are corrected to their true spatial coordinates based upon correction information stored in the system.

13 Claims, 11 Drawing Figures

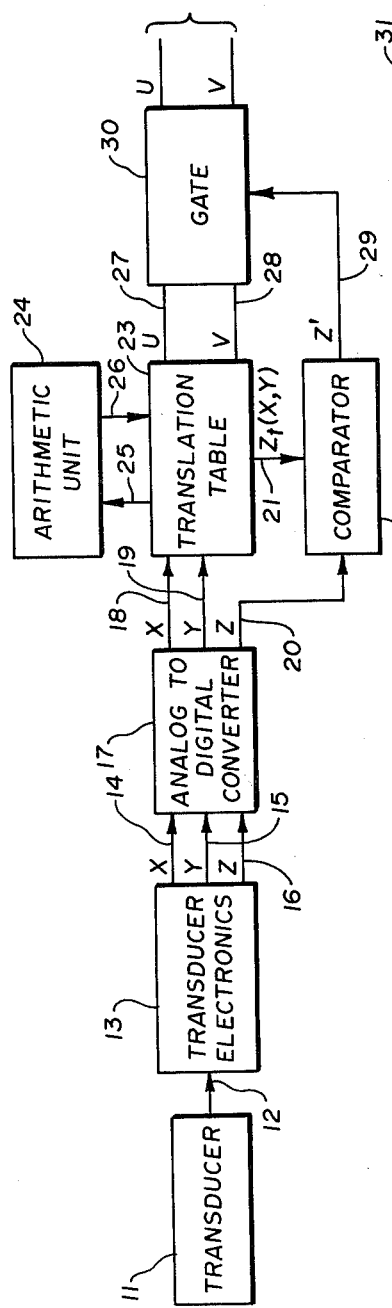
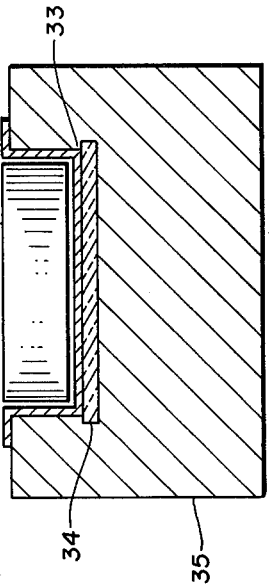
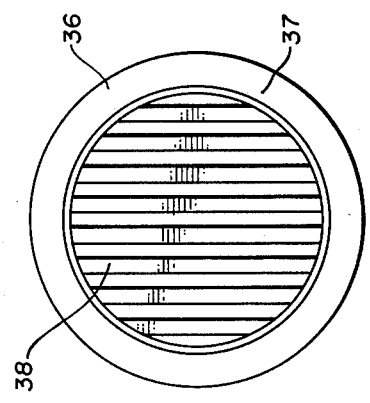
Fig.1
Fig.3
Fig.2
Fig.4

RADIATION SIGNAL PROCESSING SYSTEM

BACKGROUND OF THE INVENTION

This is a continuation of U.S. patent application Ser. No. 862,889 filed Dec. 21, 1977 and now U.S. Pat. No. 4,212,061.

This invention relates to radiation energy detectors and particularly to radiation transducer systems for surveying and precisely locating radiation sources within the human body.

Nuclear medicine is one of the most rapidly developing fields of clinical investigation. The term deriving from its origin in nuclear physics involves administration by injection into a vein of a small dose of radioisotope (a radioactive substance emitting gamma rays). The bloodstream distributes the dose throughout the body and a suitably sensitive transducer records a history of this distribution.

Areas of the body having high "uptake" of the isotope or a rich blood supply show up as bright or highly illuminating sources while conversely those of low "uptake" or blood supply appear dark. In this manner any portion of the body or a specific organ may be subjected to clinical investigation in a safe, reliable and non-invasive manner.

The device most frequently employed in nuclear investigation is a radiation transducer having a scintillation crystal (i.e. one that emits light photons proportionately to received radiation energy quanta). A plurality of phototubes in close optical communication with the crystal generate electrical signals responsive to the emitted light. U.S. Pat. No. 3,011,057, incorporated herein by reference, discloses a radiation imaging device generally referred to as an "Anger" (inventor's name) or gamma ray camera.

A scintillation camera of this type produces a picture of the isotope distribution by detecting individual gamma rays passing through a suitable collimator and striking the crystal. Electronic circuitry interprets and translates the phototube outputs into orthogonal (X,Y) coordinates and a third signal (Z) representative of the resultant camera signal output proportional to the energy level for each gamma ray event. If the energy Z signal is of acceptable magnitude i.e. falling with selected high and low values (Z window) the event is recorded and an image point is depicted in a two dimensional matrix in accordance with its coordinate position. Ordinarily the positional coordinate and energy level signals are analog but through well known techniques may be converted to their digital equivalents.

With advances in nuclear medicine and increase use as a diagnostic tool, attempts are being made to acquire increased and improved information from gamma cameras e.g. in the recognition of small tumors, measurement of heart function and dimensions etc. Unfortunately with this effort the inherent non-linearities of camera design and construction i.e. spatial distortion of image points, become more recognizable and deleterious. It is further true that with newer camera designs intended to improve camera spatial resolution both non-linearity and non-uniformity of image (the non-uniform response of camera output signal to a flood field source providing substantially uniform radiation across the camera field) have increased rather than diminished.

To obviate these inherent sources of error the prior art discloses various corrective measures. U.S. Pat. No. 3,745,345, incorporated herein by reference, determines the magnitude of camera non-linearity for a number of specific accurately located phantom radiation image points. From this, X and Y increments are derived and stored for employment in correcting camera signals either on-line or after the original distorted image has been located in core for subsequent display. While this technique potentially introduces some degree of improvement it has not sufficiently accomplished its purpose as to warrant its use and unfortunately apparently adds artifacts to the final image. Moreover the calibration technique of this patent is difficult and laborious to accomplish with any degree of precision and accuracy. It is further important to note that this prior art system completely ignores differences in Z (energy level) signal, as a function of the source position i.e. the Z signal output responsive to a point source of radiation at a particular position on the camera face, as will be made clear this is of significance.

U.S. Pat. Nos. 3,937,964; 3,980,886 and 4,001,591 all present other approaches toward increasing resolution (ability to recognize radiation sources) and avoidance of non-linearity, but none presents a system with the economy, reliability and capability for such purpose as that contained in the present novel concept. Other published scientific papers disclosing information pertinent to this subject and concerned with possible corrective measures are "Online Digital Methods for Correction of Spatial Energy Dependent Distortions of Anger Camera Images," Dennis Kirch, Leonard Shabason, Michael LaFree, and Gerry Hine and "Quantitation Studies with the Gamma Camera after Correction for Spatial and Energy Distortion" by F. Saussaline, A. Todd-Poknopek and C. Raynaud.

It is therefore an object of this invention to provide a radiation transducer imaging system having high image resolution with minimal spatial non-linearity and signal non-uniformity. Another object of the invention is to provide a system wherein each detected energy event is corrected to its true spatial location. Another object of the invention is to provide a system in which event detection is controlled as a function of spatial location. Another object is to produce a gamma ray detection system having uniform point source response and enhanced resolution. Yet other objects of the invention are to provide means for calibrating a radiation imaging system and methods for accomplishing the foregoing tasks.

SUMMARY OF THE INVENTION

The present invention derives true position information for radiation events detected by suitable transducers and in particular Anger-type radioisotope cameras producing positional information by digital means and methods. The prior art has either relied on analog processing approaches, or as in U.S. Pat. No. 3,745,345 digital means which have not proven adequate. In this system true energy event position information is derived by calibration and placed in a translation table for later call up, this data may be periodically updated to account for longterm changes in photomultiplier tubes or other camera components which are deleterious to image linearity and quality.

Determination of true coordinates for incoming events corrects for spatial non-linearities producing a distortion-free image with decreased field non-uniformities. The system may also incorporate a spatially varying Z energy signal window to compensate for inherent signal response variations across the detector face of the camera and to allow for detection of selected energy event signals e.g. only Compton recoil events if desired. This reduces field non-uniformity and permits the setting of energy acceptance criteria to maximize rejection of noise resulting in less signal ambiguity and enhanced image contrast.

In furtherance of the foregoing and to obviate prior art problems, in accordance with one aspect of the invention there is provided a radiation imaging system having a radiation transducer for producing signals relative to position coordinates of detected radiation events. The system includes means for converting the analog positional coordinate signals of the transducer to their plural bit digital equivalents and also means for storing true spatial coordinate positions for selected detected radiation events corresponding to their transducer position coordinates. The true spatial coordinate position of each detected event not corresponding to the selected events is interpolated in the intervals between the stored true spatial coordinates.

Another aspect of the invention involves means for determining the response of the transducer to each received energy event and means for modifying system response for a plurality of transducer coordinate locations.

And in accordance with another aspect of the invention a radiation imaging system is calibrated to minimize spatial non-linearities. A phantom image of accurately known dimension and position is presented to the transducer. The coordinate location signals of the transducer are compared to the calibration image and corrected coordinates are derived which corrected coordinates are then used to interpolate the true location of subsequently detected events.

Other objects and aspects of the invention will become clear upon consideration of the detailed description of the invention in conjunction with the following drawings:

BRIEF DESCRIPTION OF THE DRAWINGS

FIG. 1 is a functional block diagram for the system of this invention.

FIG. 2 is a plan view of a calibration plate.

FIG. 3 is a schematic cross-sectional view of a gamma camera with a calibration plate mounted thereon.

FIG. 4 is a representation of a typical word representing the location and level of a detected radiation event.

DESCRIPTION OF THE PREFERRED EMBODIMENT

Figure 6:
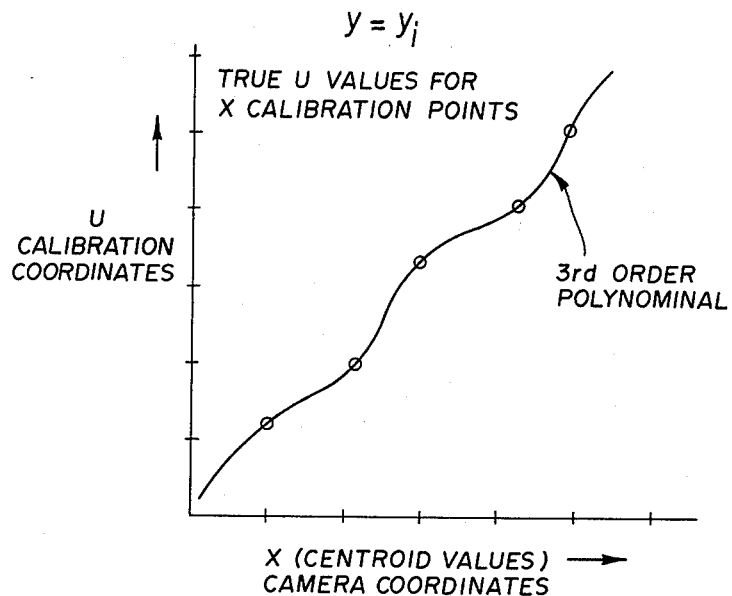
FIG. 6 is a typical best fit analytical polynomial curve for detected calibration points.

Standard gamma cameras produce three analog signals X, Y and Z. The first two are precise position coordinates of each event detected by the camera and the Z signal is a measure of the total light output from all photomultiplier tubes optically communicating with the scintillation crystal for the same detected event. The preferred method and embodiment of the invention transform these X, Y values into true coordinate U, V values respectively. Due to inherent camera and circuitry imperfections this transformation is not linear and requires non-linear correction throughout the different regions of camera field of view.

The X and Y camera coordinates are each non-linear functions of both U and V, the true spatial coordinates. This results in introducing curvature into camera image lines which theoretically should be perfectly horizontal or vertical. As is hereinafter described in detail the general corrective approach is to map out position coordinates (X, Y) of a source at known real positions in the camera field of view (known U, V values) with the spacing of these coordinate positions being sufficiently close to adequately represent the distortions which actually occur. Once this data is accumulated, mathematical fits are made to a series of one-dimensional cubic spline functions characterized by unique sets of four coefficients valid within the intervals between any adjacent calibration image coordinates. Hence these fits present a detailed record of actual camera analog signal variance and distortion.

Referring now to FIG. 1, which assumes interconnection with a computer, the radiation imaging system of the present invention is depicted in functional block diagrammatical form. Transducer 11 is a gamma camera similar to that described in U.S. Pat. No. 3,011,057, and detects radiation events emanating from an external source. Camera output signal 12 is operated on by camera electronics 13 to provide precise orthogonal spatial coordinates X 14 and Y 15 and energy level signal Z 16. These analog signals are then digitized in analog to digital converter 17 producing twelve bit X and Y words 18, 19 respectively, and an eight (8) bit Z signal.

Coordinate signals X, Y are corrected to their true coordinate U, V, 27, 28 values respectively by accessing translation table 23, rectangular matrix arrays containing U, V values addressed by their respective corresponding X, Y coordinates, and the performing of interpolation routines in arithmetic unit 24. Processor signals 25, 26 represent information going into and out of arithmetic unit 24 during the performance of specifically called up routines. Translation table 23 also furnishes selected energy threshold signal $Z_t$ 21 for the particular X, Y coordinates of detected radiation events. The energy level of Z signal 20 is compared with $Z_t$ 21 in comparator 22 and if found within the appropriate range, i.e. between acceptable limits gate signal Z' 29 is generated and gate 30 allows each acceptable energy event to be recorded and displayed at corrected coordinates U, V.

Prior to operating in the described manner certain calibration operations must be performed to furnish necessary correction data for storage in the system. To replace the tedium and inaccuracies involved with moving point sources of radiation to provide calibration images, it has been found most advantageous to employ calibration plate 36 as shown in FIGS. 2 and 3. Plate 36 provides a bar or line phantom image when flooded with a radiation source 31 such as Technetium-99m or other suitable isotope emitting gamma rays 32 effectively focused at infinity. It consists of a lead plate approximately $\frac{1}{8}''$ in thickness and 30 cms in diameter to cover the entire effective face area of camera 35. A plurality of approximately 18 to 20 lines or gaps 38 are formed in plate 36, each line having dimensions selected so that its apparent width is determined primarily by spatial resolution of the camera, viz, a width of approximately 3 mm and center to center spacing of approximately 15 mm. Flange 37 allows mounting of plate 36 in intimate contact with scintillation crystal 34 separated only by an aluminum plate approximately $\frac{1}{8}''$ thick. Thus it presents to the camera a phantom radiation image of a plurality of lines or bars the true spatial positional coordinates of which are known with a high degree of accuracy and precision. 90° rotation of the plate 36 provides cross axis line images and 180° rotation transversely displaces each line by $\frac{1}{2}$ its center to center spacing thereby presenting a new calibration image if more data is necessary or desirable.

Figure 5:
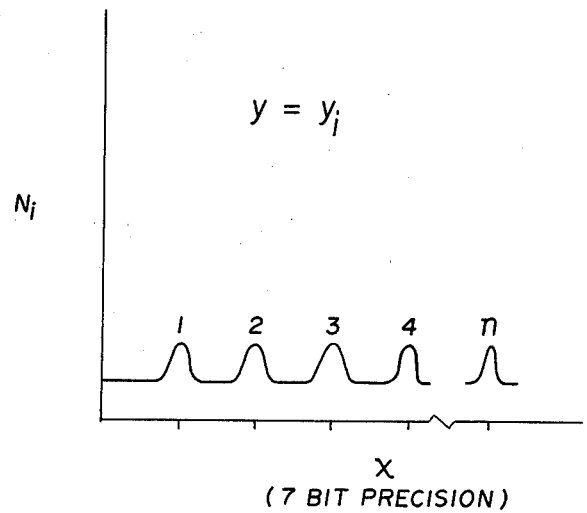
FIG. 5 is a typical distribution of X coordinate for a selected Y coordinate for the calibration image.

With plate 36 in position, X, Y signals are generated for each energy quanta or gamma ray event detected by the camera crystal and digitized in ADCs 17. Assuming lines 38 of plate 36 to be in a substantially vertical orientation, the image is analyzed in 64 equally spaced orthogonal profiles or Y positions. Selecting a profile $Y = Y_i$ as shown in FIG. 5, a distribution of events is obtained relative to each image line 1 through N. The X coordinate of each peak centroid is determined with a 7 bit precision (it should be understood the invention is not limited to level of precision employed) and referring to FIG. 6 are plotted against the known true coordinates U of the calibration image. X coordinates are chosen as the independent variable so that U may be entered with translation table 23 as a function of the 64 predetermined values of X and Y $[U = U(X_i, Y_i)]$.

An analytical polynomial expression is generated to describe and represent event coordinates between calibration intervals, preferably but not limited to a cubic spline polynomial expansion. Standard routines well known to those of ordinary skill in the art ("Elementary Numerical Analysis an Algorithmic Approach" by Conte and de Boor, 2nd Ed. 1963 P CUBIC Fr. p 234, CALCCF Fr. p. 235, SPLINE Fr. p 238) are employed to accomplish this task. A first routine determines a smooth best fit 3rd degree equation for each interval between $X_c$ calibration coordinates. A second routine provides a U value for every predetermined X coordinate preferably numbering 64.

Figure 7:
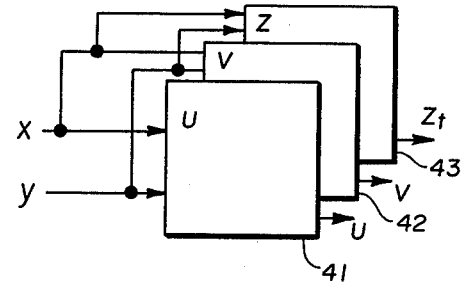
FIG. 7 is a schematic representation of three matrix arrays for the X, Y and Z correction values.

In the preferred embodiment after repeating for 64 values of $Y_i$, the process is repeated in a cross axis mode to develop V values $[V = V(Y_c, X_i)]$ for 64 $X_i$ coordinate profiles and $Y_c$ values. Each predetermined X and Y coordinate is described by (6) MSB's (most significant bits) and used to construct separate U and V 64×64 rectangular matrix array translation tables as shown in FIG. 7. Construction of tables 41, 42 permits storage of (U, V) true spatial coordinates addressed or accessed by the predetermined X, Y coordinates so that the spatial coordinates of detected radiation events may be translated to their true (U, V) location when subsequent to calibration the system is employed in clinical study.

To summarize, after plate 36 is mounted to the camera, the calibration procedure might be carried out in accordance with the following steps:

1. Select a pair of ADCs values $(X_i, Y_j)$ for which corresponding entry in the tables is to be determined.

2. For each given row in the image corresponding to $Y_i$, the data represents a one-dimensional profile through the image with event peaks at each line (see FIG. 5).

3. The centroid $X_c$ of each peak is found using a least-square Gaussian fit. This provides $X_c$ values for the uniformly spaced U values of the calibration image.

4. Spline fit this data to derive a relation of $U = ax^3 + bx^2 + cx + d$ and based on this determine U values for the 64 predetermined values of X.

5. Step through all 64 values of $Y_i$ performing steps 2 through 4.

6. Repeat the procedure with the image rotated 90° and derive a best fit expression of $V = ey^3 + fy^2 + gy + h$ then step through all 64 values of $X_i$ and enter the entire spatial corrective data into the translation tables i.e. U and V values as functions of 64 X, Y coordinates location in the rectangular matrix arrays.

Figure 8:
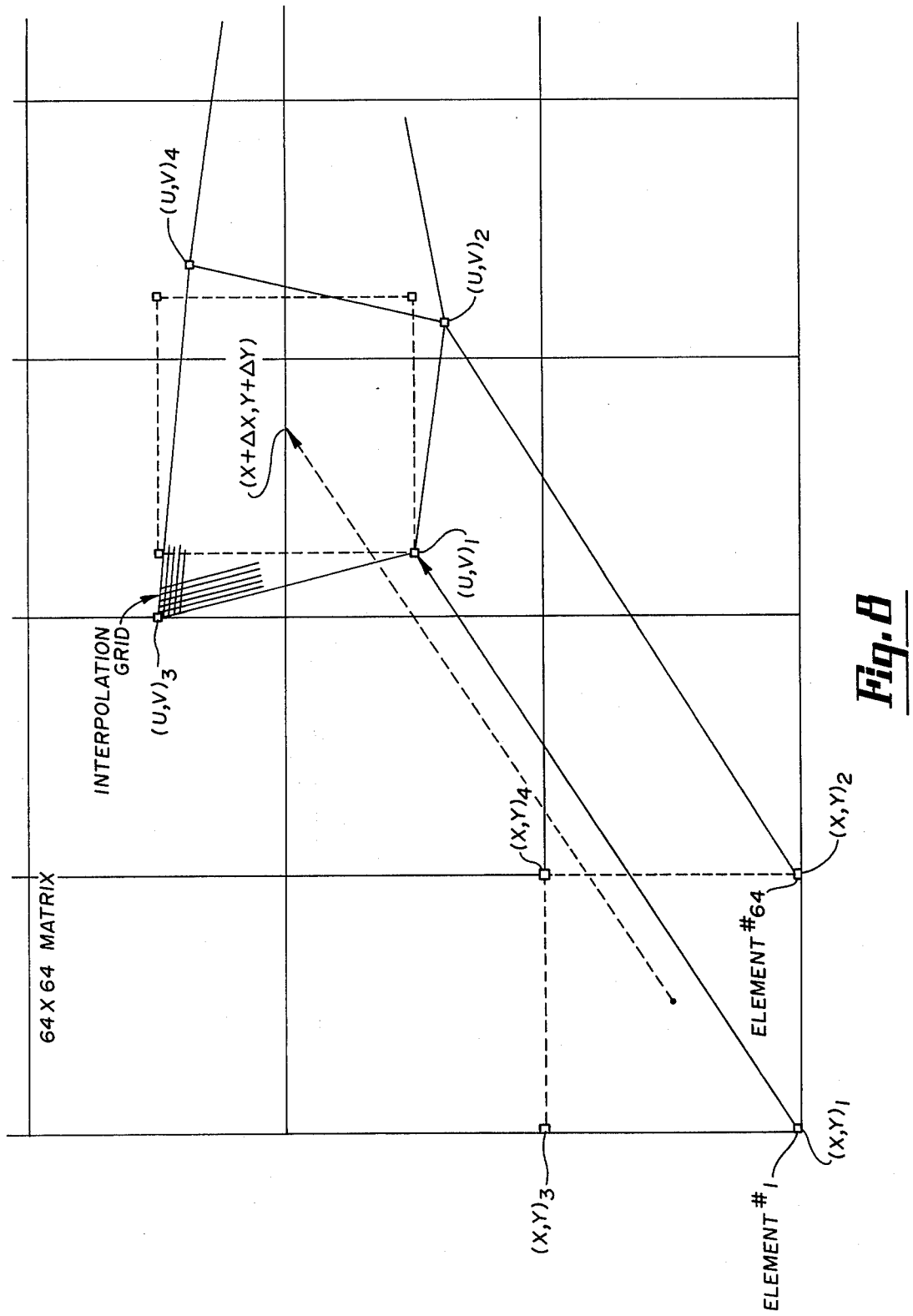
FIG. 8 is a diagrammatic representation of an idealized coordinate correction of the present invention compared to a prior art correction.

With true spatial coordinate positions U, V relative to event coordinates (X,Y) stored in 64×64 matrix translation tables 41, 42 of FIG. 7, the system may be used to acquire and correct clinical information obtained in an actual study. Referring to FIG. 8, 12 bit precision X and Y coordinate words are generated by ADCs 17 for each event. The 6 of $(X, Y)_1$ MSBs, see FIG. 4, are used to access translation tables 42, 43 obtaining the corresponding true (U, V) coordinates for such position and for each next higher coordinate $(X, Y)_{2-4}$ position in the 64×64 matrices. The translation of these coordinates from an uncorrected X, Y mapping to true coordinates U, V mapping is shown in solid outline. If succeeding translated corrected elements of the image events were shown they would form a contiguous mosaic without overlapping or voids.

Upon determination of the U, V coordinates and assuming a linear relationship in the intervals, a linear proportional interpolation is performed using the 6 LSBs (least significant bits) of each X and Y coordinate to find the precise true spatial (U, V) coordinates corresponding to the (X, Y) apparent spatial coordinates of the detected events occurring intermediate the stored coordinates of the matrices. A typical linear interpolation would proceed as follows:

1. U, V coordinates of corner elements 1 through 4 (the element corresponding to the (X, Y) MSBs of the event and the next succeeding higher coordinates of the matrix) are accessed.

2. Using the (X, Y) LSBs of the event proportionality coefficients are determined in accordance with the following:

$A = U_1 + (U_2 - U_1) \times (LSB)/64$
$B = V_1 + (V_2 - V_1) \times (LSB)/64$
$C = U_3 + (U_4 - U_3) \times (LSB)/64$
$D = V_3 + (V_4 - V_3) \times (LSB)/64$ 3. Derive precise true positional coordinates, (U, V) for the event, $U = A + (C - A) Y (LSB)/64$ and $V = B + (D - B) Y (LSB)/64$ are derived Note: proportionality constant 64 corresponds to the precision of interpolation i.e. 6 LSBs and the invention is not limited to this precision.

In this manner the true spatial coordinate position is determined for each event and camera image non-linearities and non-uniformities decreased accordingly. In this manner the invention effectively achieves the precision of correction associated with a 4096×4096 translation table with the economy and ease of calibration associated with a 64×64 matrix.

It is important to realize that the system of the invention is not limited to linear interpolation between the stored U, V values but may be readily modified to determine U, V values in accordance with any non-linear relationship if thought to better define true image position. For example, it may be recalled that during the calibration procedure coefficients were determined to describe the intervals between each camera coordinate corresponding to a best fit cubic spline polynomial expansion. These same coordinates may be stored with respect to each element in the 64×64 translation table arrays 41, 42 and utilized in arithmetic unit 24 to calculate the U, V coordinate relative to the LSBs of each event. However, experience indicates that using a 64×64 matrix array, linear interpolation provides sufficient accuracy for determination of true coordinate determination.

Again referring to FIG. 8 an important distinction over the prior art may be drawn. Heretofore as described in U.S. Pat. No. 3,745,345, depending on the bit precision desired $\Delta X$ and $\Delta Y$ are stored corresponding to matrix elements determined by the bit content of X, Y coordinates of the detected event i.e. the correction matrix array corresponds in capacity to the bit precision of the coordinates. As indicated by the dotted line translations, these correction factors are applied to the X, Y values resulting in a shift of all events located within the element to a new $(X+\Delta X, Y+\Delta Y)$ location. Thus, for the prior art to achieve the same degree of precision as the present invention it would be necessary to employ a 4096×4096 matrix array for the storage of correction factors. This invention achieves the same result by effectively using a fine interpolation grid superimposed on the 64×64 translation table matrix. When coarser grids are used in the prior art non-linearity is only partially corrected and image artifacts may be produced by the imprecise location of events and the possible overlapping of transformed elements or voids therebetween.

Figure 9:
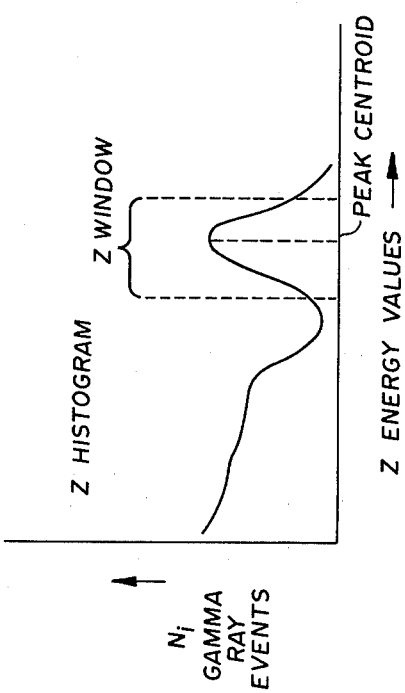
FIG. 9 is a typical energy histogram for a radiation transducer.

As previously indicated, Z signal variation is important from a number of aspects, principally involved with resolving only radiation events of interests, non-uniformity of image (it is recalled that source illumination is significant in clinical evaluation) and resultant spatial errors. The present invention prevents these distortions by altering the $Z_t$ energy threshold for a plurality of contiguous camera face segments. Referring to FIG. 9, a typical energy histogram is shown for a gamma camera. Normally the peak energy content is of interest and an energy window is selected so that only those events are recorded. This is accomplished by rejecting all events not displaying a Z level between the upper and lower threshold values. It is well known that response varies with respect to spatial position of the event, hence the apparent energy content of received events is a function of their X, Y locations. If this is not accounted for there may result serious loss of information and increased signal ambiguity.

Figure 10:
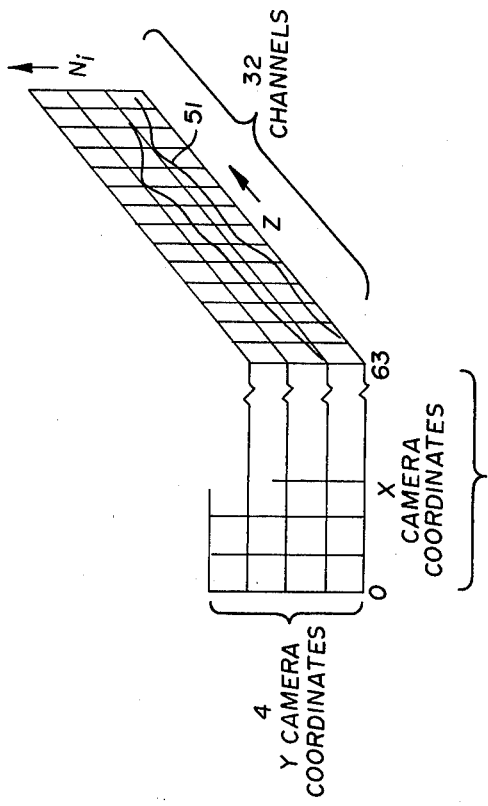
FIG. 10 is a diagrammatic representation of a plurality of energy histograms for segments of the transducer.

In order to normalize the camera Z response, a stationary point source is used to flood the camera face so that all areas receive energetic events. With reference to FIG. 10, a separate energy histogram 51 is acquired for each unique (6) bit X, Y element of 64×64 matrix array translation table 43 of FIG. 7. Due to limited computer core size histograms are acquired for only a number of Y coordinates at a time and then transferred to disc storage before the next are acquired. Preferably the number of counts $N_i$ are accumulated in a (5) bit 32 level histogram to which a standard peak search routine may be applied.

After peak determination a (16) bit word is developed for each element, (8) bits setting the low $Z_t$ value and the remaining (8) bits setting the higher $Z_t$ value (see FIG. 4). Although this window is normally associated with the half power points of the best fit Gaussian distribution, it is readily recognizable that any arbitrary limits may be established. Once set these values are placed in the Z translation table normally a 64×64 matrix array and accessed by the MSBs of each event.

When one realizes the necessity of detecting all significant events in performing clinical studies, the importance of Z normalization can be appreciated. By shifting and/or narrowing the $Z_t$ window, one is able to not only maximize the detection of significant information but minimize recording of unwanted events.

Figure 11:
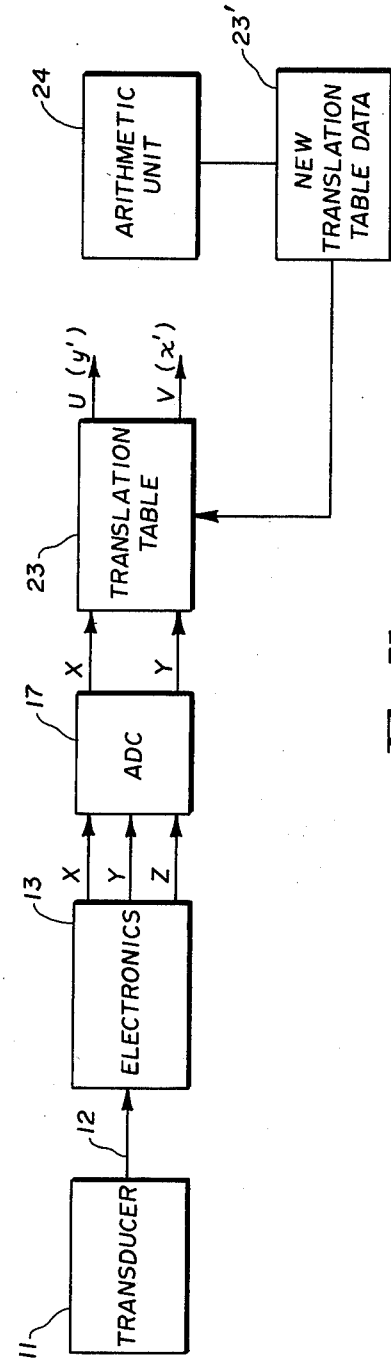
FIG. 11 is a diagrammatic representation of the system when used to iteratively correct image non-linearities.

Referring to FIG. 11, should the system require recalibration due to changes in coponents etc, this may be accomplished by the substituting of translation table U, V values as the camera's (X, Y) ADC signals for selected $(X_i, Y_i)$ coordinates thereby reducing the required degree of correction. This iterative approach may also be used during initial calibration to further reduce any remaining uncorrected non-linearities. It has been noted that around the peripheral limits of the camera face some gross non-linearities tend to remain after calibration. It is believed this is caused by the gross distortions as well as the minimal number of calibration coordinates available in these sectors for the determination of precise U, V coordinates.

Improvement in these sectors has been obtained by recalibration using a convergent iterative process, which process utilizes the same routines available in the processor as used to perform initial calibration.

The initial coarse correction may be carried out by using the same translation table approach as in the initial procedure previously set out and treating the U, V values as X', Y' camera event coordinates. New translation table 23' derived from the calibration images provides new U', V' true position coordinates for each X', Y' pair. New table 23' however must be made accesible to the original event coordinates, X, Y, which may be accomplished as follows:

1. Pick a pair of original camera ADC values $(X_i, Y_i)$.
2. Look up the corresponding X', Y' coordinates.
3. Treating this (X', Y') pair as a camera signal, use the 6 MSBs to access new translation table 23' and establish the next higher corner points in the same manner as when originally determining true event coordinates (see FIG. 8). Then use the 6 LSBs to interpolate the true U, V value at the original $X_i$, $Y_i$ address, thereby establishing a new correction table accessible by original camera coordinates.

To briefly summarize operation subsequent to system calibration, incoming gamma events generate (X, Y) spatial coordinate values and Z energy signals. The MSBs of the X, Y coordinates are used to access or address U and V true spatial coordinate in the two translation tables respectively and the 6 LSBs are used to interpolate precise true coordinates for each event. These events are then accepted by the system only if they fall within the threshold limits established for each addressed X, Y coordinate segment of a selected matrix array. Once the events are accepted, the X, Y signals are truncated to a bit content consistent with mapping in the normally coarser display matrix.

What is claimed is:

1. An improved signal processing system for radiation imaging apparatus, comprising:
    a radiation transducer producing transducer signals proportional to the energy content of detected radiation events;
    means for storing one or more selected energy limiting values as a function of event spatial coordinates;
    means for comparing the energy content of the transducer signals of the detected radiation events to the limiting value or values corresponding to the event spatial coordinates; and
    output means for producing an output signal, said output means responsive to said transducer signals and to said means for comparing, so that only those transducer signals corresponding to one or more energy ranges related to said limiting value or values contribute to said output signal.

2. The system of claim 1 wherein there are two of said limiting values, which values define a spatially varying energy window.

3. The system of claim 1 wherein the radiation transducer is a scintillation crystal camera sensitive to radiation event quanta; the energy limiting values are stored in a matrix array in accordance with regularly spaced spatial coordinates relative to the crystal face; and the spatial coordinates of each of the detected events addresses an appropriate one of the stored limiting values for comparison with the energy content signal associated therewith.

4. The system of claim 3 including means for generating signals proportional to the spatial coordinates of the detected events and wherein the energy content signals, the energy limiting values and the spatial coordinate signals are digitized to plural bit equivalents in analog to digital converter means.

5. The system of claim 4 wherein the limiting value matrix array is a square 64×64 matrix addressed by a corresponding six most significant bit content of the spatial coordinates of the detected radiation events.

6. The system of claim 5 including means for producing a field irradiating the camera crystal, means for accumulating histograms of detected radiation events as a function of the energy content signal, and the spatial coordinates thereof for each coordinate element of the camera associated with the 64×64 matrix; and means for entering in the matrix the desired limiting values relative to matrix elements.

7. The system of claim 3 wherein:
    said transducer comprises means producing transducer signals proportional to apparent orthogonal spatial coordinates of the detected radiation events;
    said output means comprises means for storing true spatial coordinates corresponding to a plurality of predetermined apparent spatial coordinates relative to selected detected radiation events, said means for storing responsive to said transducer signal and producing an output signal representative of said true spatial coordinates; and said system further comprising
    means for interpolating the true spatial coordinates of the detected radiation events located intermediate the stored true spatial coordinates, said means for interpolating cmmunicating with said means for storing.

8. The system of claim 7 wherein each orthogonal coordinate of the stored true spatial coordinates corresponds to the spatial coordinates of the limiting value matrix array and are each stored in second and third matrix arrays respectively.

9. A method for calibrating a scintillation crystal camera with respect to the energy content of detected radiation events, comprising the steps of:
    irradiating the entire camera crystal;
    accumulating the histograms of the detected radiation events as a function of predetermined apparent spatial coordinate position and magnitude;
    selecting desired limiting values for recognizing the detected events as a function of the histograms for each of the apparent spatial coordinates; and
    storing the selected limiting values in accordance with the apparent spatial coordinates associated therewith.

10. The method of claim 9 wherein the predetermined spatial coordinates form a regular rectangular matrix array relative to the camera crystal.

11. The method of claim 10 wherein the signals are expressed as plural bit digital equivalents and the matrix is a 64×64 square array.

12. A method for normalizing a scintillation crystal camera response signal with respect to the energy content of detected radiation events, comprising the steps of:
    irradiating the entire camera crystal;
    accumulating the histograms of the detected radiation events as a function of regularly spaced predetermined apparent spatial rectangular coordinate position and energy magnitude;
    selecting desired limiting values for recognizing the detected events as a function of the histograms for each of the apparent spatial coordinates;
    storing the selected limiting values in a matrix array in accordance with the apparent spatial coordinates associated therewith; and
    comparing the response signal associated with each of the detected events with the limiting value associated with the apparent spatial coordinate of the event as stored in the matrix, and recognizing the response signal if the energy content of the detected radiation event has a predetermined relationship to said limiting value.

13. The method of claim 9 further including the steps of:
    exposing the camera to a uniform field image having a plurality of parallel radiation lines,
    accumulating energy events for each given row of the image corresponding to a selected plurality of coordinate axes normal to the image lines, thereby representing a one-dimensional profile with radiation event peaks coinciding with the line locations;
    determining centroid coordinate values associated with the peaks associated with each of the profiles, thereby providing apparent spatial coordinates associated with the true spatial coordinates of each of the line profiles;
    fitting the profile data to a non-linear polynomial expression describing the true spatial coordinates as a function of the apparent spatial coordinates for each of the profiles and accumulating the true values in accordance with predetermined apparent coordinates; and
    rotating the image 90° and repeating the steps of exposing, accumulating, determining, and fitting and accumulating for a selected plurality of coordinate axes normal to the lines of the rotated image.

* * * * *